(12) United States Patent
Winzinger

(10) Patent No.: US 10,710,275 B2
(45) Date of Patent: Jul. 14, 2020

(54) CONTAINER TREATMENT SYSTEM AND AUTOMATIC EXCHANGE MACHINE

(71) Applicant: KRONES Aktiengesellschaft, Neutraubling (DE)

(72) Inventor: Frank Winzinger, Regensburg (DE)

(73) Assignee: KRONES Aktiengesellschaft, Neutraubling (DE)

(*) Notice: Subject to any disclaimer, the term of this patent is extended or adjusted under 35 U.S.C. 154(b) by 70 days.

(21) Appl. No.: 16/037,211

(22) Filed: Jul. 17, 2018

(65) Prior Publication Data

US 2018/0326623 A1   Nov. 15, 2018

Related U.S. Application Data

(63) Continuation of application No. 15/460,400, filed on Mar. 16, 2017, now abandoned, which is a
(Continued)

(30) Foreign Application Priority Data

Oct. 28, 2011   (DE) .................. 10 2011 054 890

(51) Int. Cl.
*B29C 49/28*     (2006.01)
*B29C 49/42*     (2006.01)
(Continued)

(52) U.S. Cl.
CPC .............. *B29C 31/006* (2013.01); *A61L 2/26* (2013.01); *B23Q 3/15526* (2013.01);
(Continued)

(58) Field of Classification Search
CPC ....... B29C 49/28–40; B29C 2049/4856–4861; B29C 49/6463; B67C 2003/221;
(Continued)

(56) References Cited

U.S. PATENT DOCUMENTS 4,344,221 A   8/1982 Pagani
4,890,306 A   12/1989 Noda
(Continued)

FOREIGN PATENT DOCUMENTS

EP   0985633 A1   3/2000
EP   1132334 B1   6/2000
(Continued)

OTHER PUBLICATIONS

DE102011054890.4—German Search Report for Application filed Jun. 13, 2012.
(Continued)

*Primary Examiner* — Erica E Cadugan
(74) *Attorney, Agent, or Firm* — Simmons Perrine Moyer Bergman PLC

(57) ABSTRACT

A container treatment system (1, 13) that has at least two working areas (AP). Each of the working areas (AP) respectively comprises at least one exchangeable working tool (2) and/or one adaptable format part. Furthermore, the container treatment system (1, 13) comprises at least one automatic exchange machine (10) which is movable, in particular drivable, to the at least two working areas (AP), which automatic exchange machine (10) can be connected selectively to any of the respective working areas (AP), in particular using centering means (22, 32), and which automatic exchange machine (10) comprises tools for exchanging the working tools (2) and/or for adapting the format parts of the respective working area (AP). The invention further relates to an automatic exchange machine (10) for exchanging working tools (2) and/or for adapting the format parts of at least two different working areas (AP) of a container treatment system (1, 13).

20 Claims, 9 Drawing Sheets

Related U.S. Application Data continuation of application No. 14/351,953, filed as application No. PCT/EP2012/069054 on Sep. 27, 2012, now abandoned.

(51) Int. Cl.

| | |
|---|---|
| *B29C 49/78* | (2006.01) |
| *B23Q 3/155* | (2006.01) |
| *A61L 2/26* | (2006.01) |
| *B65B 59/02* | (2006.01) |
| *B65B 59/04* | (2006.01) |
| *B67C 3/22* | (2006.01) |
| *B29C 31/00* | (2006.01) |
| *B65C 9/00* | (2006.01) |
| *B29C 49/64* | (2006.01) |
| *B29C 49/36* | (2006.01) |
| *B29C 49/48* | (2006.01) |

(52) U.S. Cl.
CPC ............ *B29C 49/36* (2013.01); *B29C 49/42* (2013.01); *B29C 49/4252* (2013.01); *B29C 49/6463* (2013.01); *B29C 49/78* (2013.01); *B65B 59/02* (2013.01); *B65B 59/04* (2013.01); *B65C 9/0062* (2013.01); *B67C 3/22* (2013.01); *A61L 2202/10* (2013.01); *B23Q 3/15503* (2016.11); *B23Q 3/15539* (2016.11); *B23Q 3/15573* (2013.01); *B23Q 2003/15537* (2016.11); *B29C 2049/4858* (2013.01); *B67C 2003/221* (2013.01); *Y10T 483/138* (2015.01); *Y10T 483/165* (2015.01); *Y10T 483/17* (2015.01); *Y10T 483/1729* (2015.01); *Y10T 483/1845* (2015.01)

(58) Field of Classification Search
CPC ........ B67C 7/0073–7/0086; A61L 2/00; A61L 2/26; Y10T 483/165; B23Q 2003/15537
USPC ............... 425/182–196, 522–541; 483/7–11, 483/58–68, 901, 15
See application file for complete search history.

(56) References Cited

U.S. PATENT DOCUMENTS

| | | |
|---|---|---|
| 5,339,597 A | 8/1994 | Naka et al. |
| 5,394,975 A | 3/1995 | Bernhard |
| 5,833,902 A | 11/1998 | Coxhead et al. |
| 6,083,146 A | 7/2000 | Earley |
| 2001/0056013 A1 | 12/2001 | Cook |
| 2008/0202681 A1 | 8/2008 | Spatafora |
| 2009/0178264 A1 | 7/2009 | Stoiber |
| 2010/0152883 A1 | 6/2010 | Achhammer et al. |
| 2011/0040403 A1 | 2/2011 | Langanki et al. |
| 2011/0052744 A1* | 3/2011 | Meinzinger ........... B29C 31/006 425/183 |
| 2011/0061690 A1* | 3/2011 | Seger ..................... B29C 33/72 134/137 |
| 2011/0078979 A1 | 4/2011 | Hutter |
| 2013/0224323 A1 | 8/2013 | Meinzinger et al. |
| 2013/0291897 A1 | 11/2013 | Lohrke |
| 2013/0309343 A1 | 11/2013 | Stoiber et al. |

FOREIGN PATENT DOCUMENTS

| | | |
|---|---|---|
| JP | 362044337 | 2/1987 |
| JP | 8001709 A | 1/1996 |
| WO | 2008145345 A1 | 12/2008 |

OTHER PUBLICATIONS

PCT/EP2012/069054—ISR Search Report for Application filed Jan. 2, 2013.

First Office Action from Chinese National Phase of PCT Application, Application No. 201280053146.1, Document Serial No. 2014123100452500 dated Jan. 6, 2015.

Merriam-Webster's Collegiate Dictionary, 10th Ed., copyright 1998, pp. 62 and 53, re the definition of "arm".

Merriam-Webster's Collegiate Dictionary, 10th Ed., copyright 1998, pp. 1013, re the definition of "robot".

* cited by examiner

Fig. 10a a robot comprising a plurality of arms and/or gripping tools

Fig. 10b a blow molding module comprising a blowing wheel, an adjustable curve, and blow mold carriers

CONTAINER TREATMENT SYSTEM AND AUTOMATIC EXCHANGE MACHINE

CLAIM OF PRIORITY

The present application is a continuation of patent application Ser. No. 15/460,400, filed on Mar. 16, 2017, which in turn is a continuation of patent application Ser. No. 14/351,953, filed on Apr. 15, 2014, which in turn is a national stage application under § 371 of PCT/EP2012/069054, filed on Sep. 27, 2012, which in turn claims priority to DE 10 2011 054 890.4, filed on Oct. 28, 2011, all of which are incorporated by reference.

FIELD OF THE INVENTION

The present invention relates to a container treatment system and an automatic exchange machine having the features of the preambles of the claims.

BACKGROUND

Large-sized filling and/or packaging lines usually comprise a plurality of container treatment modules, for instance modules for producing containers or bottles, or for filling, closing, labeling them, etc. The individual modules need to be converted depending on the product to be manufactured. In particular, it is necessary to exchange certain working tools and/or to adapt format parts to the new product. For converting the filling and/or packaging line from product number 1 to product number 2, for instance, in order to produce a new container form, it may be necessary to exchange the blow molds in a blow molding module. It is furthermore necessary to adapt, for instance, certain format parts in the downstream filler etc. to the new container form.

For exchanging the working tools and/or for adapting the format parts of individual container handling modules, specific exchange devices are respectively provided at each module, which exchange devices supply the appropriate working tools to be exchanged or the appropriate tools for adapting the format parts. These exchange devices are equipped with the appropriate working tools or the appropriate tools according to the respective product. Depending on which working tools need to be exchanged or which format parts need to be adapted or adjusted, it is also possible that several exchange devices may be required for each module. Each of these exchange devices is required for converting only one certain working tool and/or for adapting only one certain format part in the instance of a product change. For most of the time, these exchange devices thus remain unused and stand in the way, taking up space and increasing the overall dimensions of the facility. The user needs one or more of these exchange devices for each module, resulting in high acquisition costs for the modules.

DE 4242925 A1 describes a transport device for bottle treating machines wherein a gripping device with a gripping head is provided for exchanging the working tools. The gripping device is mounted to the machine frame and controlled by means of a control device.

EP 0985633 A1 discloses a device for the automatic exchange of filling heads. It provides an equipping and exchange automaton at the lateral periphery of the container treating machine, which equipping and exchange automaton is movable into different positions and which is suitable for use in mounting component parts to and removing them from the treatment heads, bringing the component parts into a storage position, retrieving other component parts from their storage position, and connecting the component parts with the treatment heads.

It is the task of the present invention to provide a container treatment system that allows the easy and efficient exchange of working tools or the easy and efficient adaptation of format parts while at the same time effecting a better utilization of the required exchange devices.

The above task is solved by a container treatment system and an automatic exchange machine comprising the features of the claims.

SUMMARY OF THE INVENTION

The present invention relates to a container treatment system for producing and/or processing products and/or product groups. The invention further relates to an automatic exchange machine for exchanging working tools and/or for adapting format parts of a container treatment system.

The invention in particular relates to a container treatment system for producing containers, filling a preferably liquid content into these containers, closing the filled containers, labeling the containers, and/or assembling and packaging the containers in groups. Such a container treatment system commonly comprises at least two container treatment modules. This container treatment system may be, for instance, a bottle manufacturing, a bottle filling, and/or a bottle packaging facility, which, among others, comprises a heating section, a blow molding module, a labeling module, and a filler. Further modules are described with the exemplary embodiments. The container treatment system may also be a facility comprising several production lines, wherein each production line comprises at least two modules. Each of these production lines may have the same arrangement of modules. However, it is also conceivable that the at least two production lines comprise in each case different container treatment modules.

The container treatment system comprises at least two working areas in which a product change requires the exchange of working tools and/or the adaptation of format parts. A product change requires, for instance, the blow molds in a work module to be exchanged and the guide rails of a transport means, on which the blow molded and/or already filled bottles are supplied to further processing devices, to be adapted to the respective width of the bottles by adjusting the said guide rails in relation to each other.

The container treatment system comprises at least one automatic exchange machine that is movable, in particular drivable, to the at least two working areas. The automatic exchange machine can be connected selectively to the working areas of the container treatment system by centering means. The automatic exchange machine is a so-called exchange device and serves to replace the at least one working tool and/or to adapt the format part. The automatic exchange machine comprises appropriate means for this purpose.

Each of the working areas of the container handling system respectively comprises a first connection device with centering means. The automatic exchange machine, in contrast, comprises at least one second connection device with centering means. The at least one second connection device with centering means of the automatic exchange machine is formed correspondingly to each of the first connection devices with centering means of the at least two working areas of the container treatment system. The second connection device with centering means and one of the first connection devices can serve for creating a form-locking and/or force-locking connection between one of the working areas and the automatic exchange machine. In particular, this means that the mobile automatic exchange machine may be connected either to the one of the two working areas or to the other of the two working areas. The automatic exchange machine is thus not permanently assigned to one of the two working areas. The automatic exchange machine is, in particular, only connected to the container treatment system or to the container treatment module at the appropriate working area while in the exchange mode, i.e. when a container treatment system requires conversion for a product change. During production operation of the container treatment module, the automatic exchange machine remains passive or may be used at another working area of the container treatment system. It would also be conceivable to supply the automatic exchange machine with a function for assisting in the production process while the automatic exchange machine is momentarily not required or not being employed for a format change. In such a case, the automatic exchange machine may be equipped, for instance, with a buffer for bottles or with a collection capacity for bottles that were discharged from the production process.

The working areas may form part of the container treatment system or of the container treatment module. Alternatively, the working areas are not part of the container treatment system or of the container treatment module, but rather respectively form accordingly assigned docking sites in the floor of the hall in which the container treatment system is located.

The connection devices with centering means of the container treatment system are, for instance, so-called centering pins or centering cones. The automatic exchange machine comprises corresponding receptacles into which the centering pins or centering cones are inserted. A snap-lock connection, a plug connection, or the like may thereby be produced between the centering means and the automatic exchange machine. A directed, form-locking and/or force-locking connection between the automatic exchange machine and the container treatment system is thus created. The centering means serve for directly aligning the automatic exchange machine for the purpose of the exchange or adaptation process. The connection devices with centering means may also be means suited purely for data exchange only. This would include, for instance, the optical detection and self-alignment of the automatic exchange machine with the modules or the detection of a docking of the automatic exchange machine by the module, using, for instance, transponders arranged at the automatic exchange machine. An alignment dowel pin, which can be inserted into a drill hole, or it may be a stop surface or a recess in the floor may be utilized as a centering means. Other centering means that are known to the expert are also encompassed in the scope of the present invention.

The first working area may be assigned to a first module of the container treatment system, for instance to a blow molding module, and the second working area may be assigned to a second module of the container treatment system, for instance to a filler. The automatic exchange machine may thus be employed either at the blow molding module or at the filler. Alternatively, the first and the second working areas may be assigned to the same container treatment module. In the instance of a product change, the filling valves on a filler are exchanged in the first working area, for instance, while in the second working area the return air pipe is adapted. According to a further alternative embodiment, the automatic exchange machine is used at comparable modules of two production lines, i.e. the automatic exchange machine may be employed at least at the blow molding module of a first production line and at the blow molding module of a second production line. According to one embodiment form of the present invention, it is provided that the automatic exchange machines are assigned specific to the type of fittings in a manufacturing facility comprising a plurality of production lines. This means that one automatic exchange machine each is provided respectively for each type of container treatment module, in particular, one automatic exchange machine for all blow molding modules of the production line, one automatic exchange machine for all fillers of the production line, etc.

The automatic exchange machine may comprise at least two different connection devices for coupling to the different working areas. According to a preferred embodiment form, however, it may be provided that the automatic exchange machine comprises a so-called universal connection device and that the working areas each comprise corresponding universal connection devices.

The automatic exchange machine preferably comprises at least one magazine for working tools, which magazine may respectively be equipped with different working tools. It is alternatively or additionally possible for the automatic exchange machine to comprise tools for exchanging the working tools and/or for adapting the format parts, wherein these tools may also be exchanged. The magazine may be designed for the working tools and/or the tools to be stored either in a hanging or in a standing position. The automatic exchange machine is required for exchanging the blow molds of a blow molding module, for instance. Such an exchange is only necessary when there is a product change so that the automatic exchange machine is not needed for most of the time. The automatic exchange machine may be converted by the operator of the facility or it may be automatically converted, i.e. equipped with new working tools and/or tools and reprogrammed if required, during the times of non-operation, i.e. during the times with no exchange of working tools or with no adaptation of format parts taking place at the first working area. It is then possible to employ the automatic exchange machine at the second working area or at a further working area For instance, blow molds that are no longer needed are taken to a storage and filling valves arranged in the magazine instead, making it possible to then employ the automatic exchange machine for setting up a filler for a new product, for example. The automatic exchange machine may also comprise a plurality of magazines for different fittings or replacement parts. The automatic exchange machine may likewise comprise at least one docking station of its own, onto which other exchange equipment may dock for the purpose of replacing entire exchange magazines, for example.

The automatic exchange machine may, on the one hand, provide the necessary working tools and/or the necessary tools for converting the container treatment system. On the other hand, the automatic exchange machine may preferably provide the mechanics and/or electronics for performing the conversion of the container treatment system in the respective working area largely independently, in particular semi- or fully automatically. In particular, the automatic exchange machines may serve for transmitting updates of the operating software to the modules, for example in the instance of having to convert the container treatment system to the production of new, hitherto not yet processed bottles.

The automatic exchange machine may comprise, for instance, at least one replacement star wheel having gripping devices for gripping the appropriate working tools. In a further embodiment variant, the automatic exchange machine may be a robot comprising a plurality of arms and/or gripping tools, which are movable via axes, for performing the appropriate conversion operations. In the simplest case, this may be, for instance, an automaton with pneumatic actuators such as is known from being employed in blow molding modules. It is in particular possible to synchronize the respective drives of the treatment module and the automatic exchange machine. The drives are preferably servomotors, but synchronization by means of a gear coupling is also possible.

All working tools that are to be exchanged are preferably mounted to the container treatment modules by means of a locking mechanism that can be quickly opened or closed, for instance a snap-lock mechanism, in order to enable the working tools to be exchanged without requiring the use of further tools at the touch of a button or the like. It is alternatively possible for the automatic exchange machine to comprise appropriate tools, for instance screw driving tools or the like, for exchanging the working tools.

Apart from exchanging the working tools, the automatic exchange machine may also perform adjustments of the container treatment modules, for instance the adaptation of cam tracks for controlling certain container treatment modules.

The automatic exchange machine preferably comprises transport means. Transport means are necessary in order to enable quick transport of the automatic exchange machine to its respective points of use at the different working areas. In the simplest case, the automatic exchange machine has wheels so that an operator can manually push the automatic exchange machine to the respective working area. The automatic exchange machine may alternatively be equipped with a drive of its own. Additionally, the automatic exchange machine may be provided with its own optical detection system, for instance, enabling the automatic exchange machine to find and take the correct position at the machine by itself. According to one embodiment variant, the automatic exchange machine is intended to be moved along a system of tracks. These tracks extend at least between the first working area and the second working area of the container treatment system. In this instance, it is possible to preset the position of the automatic exchange machine by means of a control device. The automatic exchange machine is then automatically guided along the track system to the correct working area.

According to one embodiment form, the automatic exchange machine comprises a control device for automatically controlling the conversion process of the container treatment system. The control device in particular controls the exchange of the working tools at the respective working area and/or the adaptation of the format parts at the respective working area and/or the correct positioning of the automatic exchange machine at the respective working area.

The control device is programmed according to the new product specifications and the automatic exchange machine is equipped with the necessary working tools and/or the necessary tools so that the conversion operations can be performed manually, semi-, or fully automatically by means of the automatic exchange machine after coupling to the container treatment module. This means that the automatic exchange machine comprises all necessary means for automatically performing the required conversion operations or else the automatic exchange machine provides the necessary means for an operator to be able to perform the required conversion operations manually or semi-automatically.

Based on the new product specifications, the control device for instance calculates the working tools to be exchanged or the format parts to be adapted. The results of this calculation are displayed to the operator of the container treatment system by means of a display unit, for instance. The automatic exchange machine may, however, also retrieve the required working tools and/or the required tools from a storage, for instance in an automated process, arrange these working tools and/or tools in an internal magazine of its own, automatically take the correct working area at the container treatment system, couple to the container treatment system by means of the connection device in a form-locking and/or force-locking connection, and perform the appropriate exchange of the working tools or the appropriate adaptation of the format parts. The control of the automatic exchange machine may also calculate the sequence that is the least time consuming for performing the format change. The display may be used for communicating this sequence to the employees. In particular, the necessary information on occupational safety is also on file in the control device so that tasks that have to be performed simultaneously by employees cannot be hampered or endangered by the employment of the automatic exchange machine.

The automatic exchange machine may furthermore be provided with interfaces for supplying power, compressed air, and/or data to the automatic exchange machine. These connections are created manually, semi- or fully automatically on coupling the automatic exchange machine to the respective container treatment module.

According to a further embodiment form, the automatic exchange machine is connected with the container treatment system at one of the working areas and in particular coupled at a control device of the container treatment module or of the container treatment system. In this embodiment form, the automatic exchange machine receives all necessary information on the working tools that are to be exchanged and/or the format parts that are to be adapted from the module control of the container treatment module or of the container treatment system.

The automatic exchange machine may comprise sensory means for detecting working tools and/or tools. The sensor may allow the automatic exchange machine to detect, for instance, the working tools stored in the internal magazine and to select the correct working tools to install in the respective container treatment module. The automatic exchange machine may alternatively comprise sensory means for identifying the correct working tools in an external storage place. For easier detection of the working tools, RFID chips, bar codes, or other codes are applied, in particular to the tools or fittings, but also to the corresponding sections of the modules.

According to one embodiment variant, the automatic exchange machine may comprise one magazine for all types of working tools of one container treatment module. The automatic exchange machine may, for instance, be equipped with different blow molds for one blow molding module. The magazine can store the working tools (blow molds) grouped into sub-magazines according to type and retrieve the desired working tool type (blow mold type) according to the respective program. The program identifies the correct working tools (blow molds), retrieves them from the internal magazine, and installs them. It may be provided here that each working tool type is assigned a certain position in the magazine so that the correct working tools are retrieved based on their positioning in the magazine. Alternatively, it is possible to provide a detection system for this purpose. The working tools may each be equipped with an RFID chip or the like, which allows easy identification and assignment.

According to a further embodiment form, the automatic exchange machine may provide only the mechanics for exchanging the working tools that are being stored in an external magazine at the container treatment module or elsewhere. For this purpose, the automatic exchange machine is equipped, in particular, with a detection system, which detects the different working tools in an external storage, selects the correct type of working tool by means of the program, and installs it at the appropriate location into the container treatment module.

According to a further embodiment variant, the automatic exchange machine comprises a magazine holding working tools for exchange wherein more exchange parts are kept in the magazine than are actually required for converting the container treatment module. The position of a working tool in the automatic exchange machine and at the container treatment module is stored by a control device, for instance by an internal control of the automatic exchange machine or by the module control of the container treatment system, so that the automatic exchange machine can selectively retrieve the working tools from the magazine and employ them in such a manner that they are evenly used. This ensures a largely even wear and tear of the working tools. It may furthermore be provided that the automatic exchange machine comprises a sensor for detecting defective working tools and/or defective tools. On detecting defective working tools and/or defective tools, the sensor outputs a signal to the display device for the operator to identify and replace or repair the defective working tool and/or the defective tool. In an automated system, it may be provided that the automatic exchange machine automatically ejects the defective working tool and/or the defective tool and replaces it with a new working tool and/or a new tool from the storage.

During the conversion process, the container treatment module is preferably operated in exchange cycles and in particular in an intermittent, strokewise manner. In particular, the working area comprises an exchanging position. Per stroke, one blow mold, for instance, that is located in the exchanging position is retrieved from there and stored into the internal magazine of the automatic exchange machine or into an external magazine. The blowing wheel subsequently continues rotating so that the originally adjacent former blow mold now comes to be in the exchanging position. The former blow form is then exchanged. This process continues to be performed until all former blow molds have been removed from the blow molding module. In a following cycle, the new blow molds are mounted in the blow molding module in an intermittent process. Alternatively, one format part per stroke is adapted according to the new product. It may furthermore be provided that the exchange of working tools is performed in a continuous rather than an intermittent process. If it is necessary to additionally prepare the working tools, it is also possible to have the respective module perform the preparatory tasks. In the instance of a blowing wheel, it is possible to have an adjustable curve for alternating operation modes, which adjustable curve (in combination with a cam roller) allows unlocking and opening blow mold carriers with blow molds for exchange arranged in them already shortly before the blow molds are exchanged. Time can be saved in this manner, as the automatic exchange machine is not required to perform all tasks on its own. After exchanging the blow mold, a second adjustable curve would then perform the task of locking the blow mold. This function may also be performed by an adjustable double curve.

According to an alternative embodiment form, the automatic exchange machine may also perform both operations, i.e. removing the former working tool and mounting the new working tool, simultaneously in one cycle. In this instance, the automatic exchange machine in particular comprises at least one empty magazine for receiving the removed working tools and at least one storage magazine, into which the new working tools for being mounted can be filled either manually or in an automated process according to the conversion requirements for the respective container treatment module prior to being converted. This task may also be performed in a continuous process. It would even be possible to perform the process while the production is running. For this purpose, an automatic exchange machine could be placed between the infeed and the outfeed of a treatment machine, i.e. in particular in such an area of the production where no containers are treated.

While exchanging working tools or adapting format parts, it is usually necessary for machine parts of the respective container treatment module to shift and move in order to arrange the working tools or format parts into their respective proper positions for exchange. This must be performed with due consideration for the safety of the operators. In particular, the operators must be prevented from coming into contact with moving, for instance, rotating machine parts. In order to ensure the safety of the operators, the star wheels of the respective working tools that are to be exchanged are driven independently from the star wheels that are currently not being exchanged in an exchange cycle, for instance. Safety precautions may furthermore provide that the automatic exchange machine is linked to the working area in such a manner that an operator can no longer reach in between during the exchange process.

The invention furthermore relates to an automatic exchange machine for exchanging working tools and/or for adapting the format parts of at least two different working areas of a container treatment system, which automatic exchange machine is mobile so that it may be employed respectively at each of the at least two working areas of a container treatment system. In particular, the automatic exchange machine comprises the above-described features. According to the invention, the automatic exchange machine is thus employable in at least two locations or working areas of the container treatment system for the purpose of exchanging working tools and/or adapting format parts to convert the container treatment system in the instance of a product change. Preferably, it is possible to use the automatic exchange machine universally with different container treatment modules of one production line or with a plurality of productions lines arranged in one hall. This allows doing away with having to provide a specific exchange device at each container treatment module for each working tool to be exchanged or for each format part to be adapted, with such an exchange device being out of use most of the time. Multiple use significantly improves the efficiency of the automatic exchange machine by increasing utilization. To the user, this reflects in lower costs because it is not necessary to purchase an exchange device for each individual module.

While the automatic exchange machine/machines is/are performing the exchange process, the operator of the system or systems is free to see to other conversion processes that are not or cannot be performed by the automatic exchange machines.

Such an automatic exchange machine is preferably employed at a container treatment system or a container treatment module that comprises an endless conveyance means, in particular rotary modules, such as blow molding modules, fillers, etc., or modules with a circulating chain drive, for instance linear ovens etc.

The invention further relates to an automatic exchange machine for exchanging working tools and/or for adapting format parts of a container treatment system for producing products and/or product groups. The automatic exchange machine comprises a connection device with centering means and is assigned to an exchange area of the container treatment system. The exchange area of the container treatment system comprises a corresponding connection device with centering means. A form-locking and/or force-locking connection between the exchange area and the automatic exchange machine is created by connecting the two connection devices. The automatic exchange machine may alternatively be arranged in a stationary position at the container treatment system. The automatic exchange machine comprises at least one empty magazine for receiving the working tools to be removed and at least one storage magazine. The storage is filled with the working tools or with the necessary tools that are respectively required for producing or processing a certain product. This automatic exchange machine enables to simultaneously retrieve the former working tools and mount the new working tools. This means that while a former working tool is being retrieved from a first, defined position in the container treatment module, a new working tool is installed at a second position. Preferably, the retrieval of the former working tool and the mounting of the new working tool are each performed at adjacent positions or at only a few positions apart.

Such an exchange is thus performed at a blow molding module, for instance, in the following manner: First, a former blow mold is retrieved from a first position and placed into an empty magazine. Afterward, the blowing wheel rotates, advancing by one position. While the second former blow mold is being retrieved from the second position, a new blow mold is mounted in the first position at the same time. Afterward, the blowing wheel rotates, again advancing by one position. Now, the third former blow mold is retrieved from the third position and, at the same time, a new second blow mold is mounted in the second position, and so on.

According to a preferred embodiment variant, the magazines are continuously advanced, in particular rotated, and the working tools are exchanged in a continuous process. One possibility is for the automatic exchange machine to exchange the working tools at a speed that is lower than the regular production speed of the container treatment device. Ideally, however, the exchange may be performed at production speed. According to a further embodiment form, production is intended to continue without interruption during the exchange process. For this purpose, a container may be discharged on the feed conveyor or before that. Alternatively, the container treatment device skips the production of this container altogether. In this manner, it can be prevented that a container comes to stand in the gap, which is temporarily produced by removing the first working tool, so that said container would interfere with the exchange process. According to yet a further embodiment form, it is also possible to remove the working tool together with the last produced or treated container. The container then has to be discharged by the automatic exchange machine and rejected, for example.

As an alternative to or in addition to the simultaneous removal and installation, this automatic exchange machine may also retrieve the former working tools and mount the new working tools in a continuous process. Not before the first magazine is completely filled with the blow molds that are no longer needed, for instance, are the new blow molds transferred into the machine from the storage magazine and mounted in a second circuit of the machine in this alternative. In the combination of simultaneous and continuous removal and installation, the first magazine is filled with the former tools until the resulting gap has reached the second magazine, which then installs the first new tool into this first gap. That moment is the starting point of a continuous cycle for exchanging the remaining tools, wherein both the treatment carousel and the two magazine devices continuously rotate until each former tool has been removed from each station of the treatment carousel and the first magazine no longer has to retrieve any more tools. The second magazine continues working until all gaps on the treatment carousel are filled with tools. Apart from the beginning and the end of the exchange cycle, the exchange of the tools is thus performed in a simultaneous and continuous process.

BRIEF DESCRIPTION OF THE DRAWINGS

In the following passages, the attached figures further illustrate exemplary embodiments of the invention and their advantages. The size ratios of the individual elements in the figures do not necessarily reflect the real size ratios. It is to be understood that in some instances various aspects of the invention may be shown exaggerated or enlarged in relation to other elements to facilitate an understanding of the invention.

FIGS. 10*a* and 10*b* show schematically further features of the invention.

DETAILED DESCRIPTION

Figure 1:
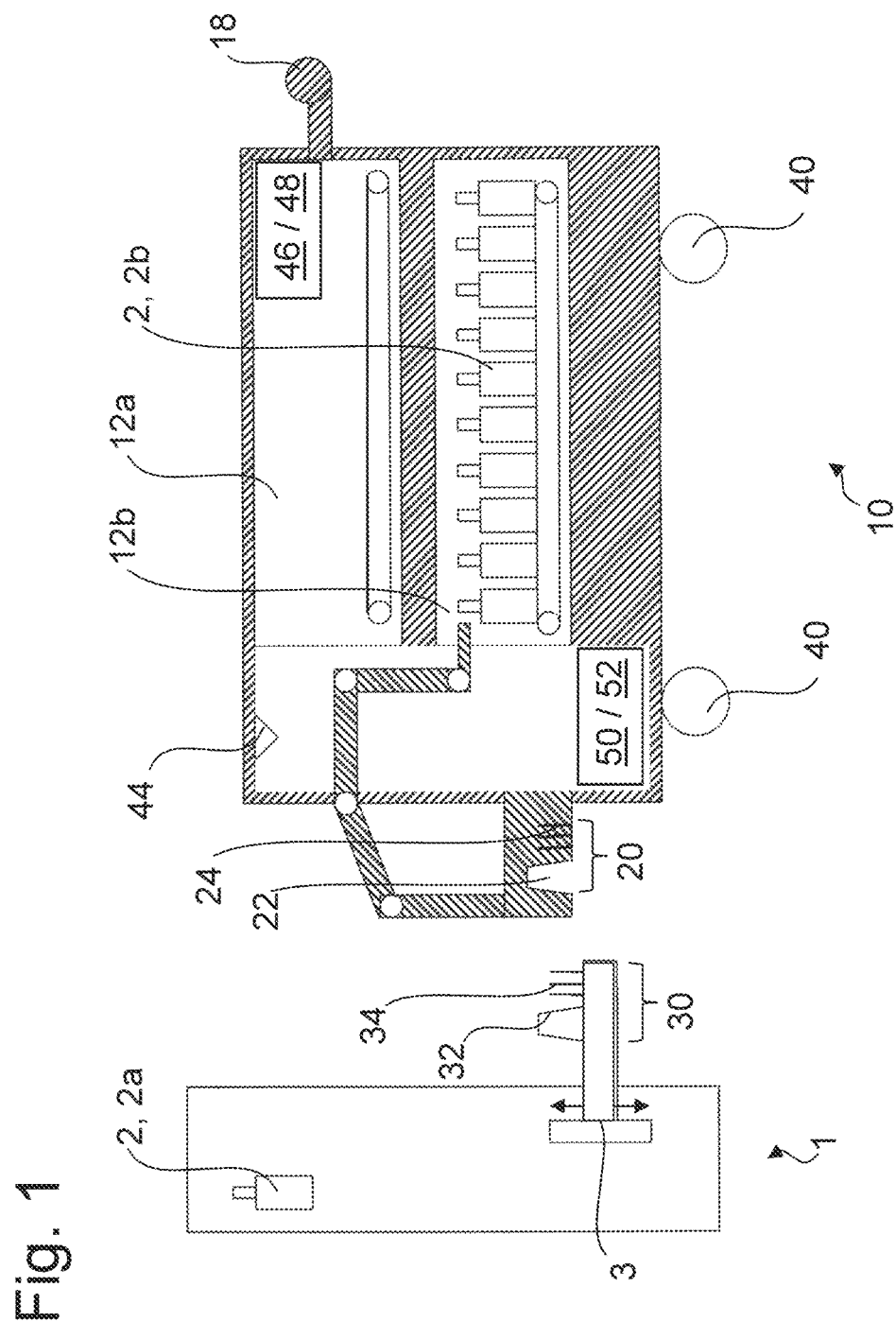
FIG. 1 shows a schematic side view of an automatic exchange machine according to the invention next to a processing device.

The same or equivalent elements of the invention are designated by identical reference characters. Furthermore and for the sake of clarity, only the reference characters relevant for describing the respective figure are provided. It should be understood that the detailed description and specific examples of the device according to the invention, while indicating preferred embodiments, are intended for purposes of illustration only and are not intended to limit the scope of the invention.

FIG. 1 shows a schematic side view of an automatic exchange machine 10 next to a processing device 1. In the instance of a product change, this embodiment variant requires the working tools 2 to be exchanged depending on the product that is being handled. The working tools 2*a* in the processing device 1 have to be exchanged for the working tools 2b, for example. The automatic exchange machine 10 comprises at least two magazines 12a, 12b, for receiving working tools 2, 2a, 2b.

The automatic exchange machine 10 comprises at least one interface 20 and the processing device 1 comprises at least one corresponding connection device 30. The interface 20 and the connection device 30 each comprise mechanical connecting elements and/or centering elements. The connection device 30, for instance, comprises at least one centering pin or centering cone 32, which inserts into a corresponding centering opening 22 of the interface 20. The automatic exchange machine 10 may thus be aligned and installed at the processing device 1 such that the automatic exchange machine 10 can immediately and properly take up work.

The interface 20 furthermore comprises electrical and/or pneumatic connecting elements 24 for connecting with corresponding electrical and/or pneumatic connecting elements 34 of the connection device 30. The interface 20 and the connection device 30 thus enable creating further connections between the automatic exchange machine 10 and the processing device 1; the automatic exchange machine 10 may, for instance, be connected with the power supply system of the processing device 1, with a control device of the processing device 1, with the compressed air system of the processing device 1, etc.

The automatic exchange machine 10 comprises wheels 40 so that it may be moved either by means of a drive of its own (not illustrated here) or manually. A push handle 18, for instance, is provided for this purpose. The automatic exchange machine 10 may furthermore be provided with a battery 50 and an own drive 52 for other necessary functions. Appropriate interfaces may also be provided to serve for supplying the automatic exchange machine 10 itself with power, compressed air and/or data.

If necessary, it may be provided for the automatic exchange machine 10, which is coupled to the processing device 1, to be lifted by means of a lifting mechanism 3 at the processing device 1 and then be moved into the correct position.

Preferably, the processing device 1 is operated in intermittent strokes in an exchange cycle with one working tool 2, 2a being retrieved per stroke. The working tool 2, 2a is subsequently arranged into the magazine 12a of the automatic exchange machine 10. The new working tools 2, 2b are, again intermittently, installed in the appropriate locations in or at the processing device 1 in a further cycle.

A sensor 44 for detecting defective working tools 2, 2a, 2b, and/or for identifying the working tools 2, 2a, 2b or the format of the working tools 2, 2a, 2b in the magazines 12a, 12b is provided in the automatic exchange machine 10. On detecting a defective working tool 2, 2a, 2b, the sensor 44 outputs an appropriate error message so that the defective working tools 2, 2a, 2b may be removed and exchanged or repaired. The error message is output to a display panel 46, for instance, which is part of a control unit 48, for instance.

Figure 2:
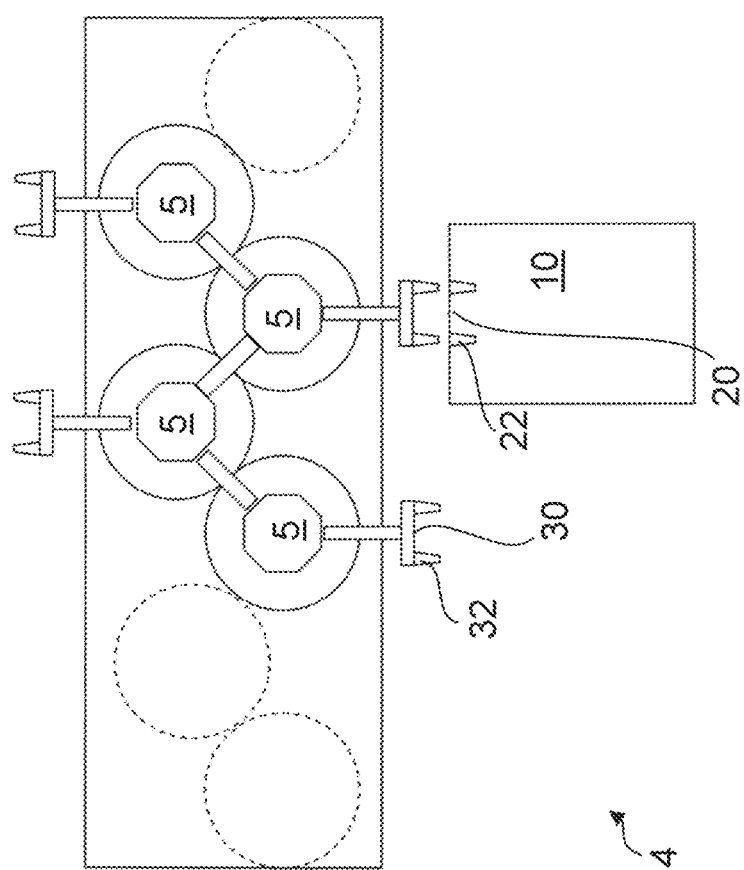
FIG. 2 shows an automatic exchange machine according to the invention being employed at a transfer device consisting of transport star wheels.

FIG. 2 shows an automatic exchange machine 10 according to the invention being employed at a transfer device 4, which consists of Monotec transfer star wheels 5. Such a transfer device 4 is used, for instance, in order to be able to variably connect individual transfer stars 5 with each other at interfaces, which are illustrated as octagons here, using struts, which are not illustrated here, and possibly in order to minimize the outer surfaces of a filling area that require cleaning. In the instance of a product change and depending on the respective type of product, transporting different types of containers by means of the Monotec transfer star wheels 5 requires the exchange, in particular, of the gripping clamps (not illustrated here) for holding the containers (not illustrated here). The Monotec transfer star wheels 5 each comprise a connection device 30 with centering bolts 32, which allow the automatic exchange machine 10 to dock onto the respective Monotec transfer star wheel 5 in order to exchange the gripping clamps (not illustrated here). Advantageously, the connection device 30 may also be arranged at the interfaces in the same manner as the struts may be arranged.

Figure 3:
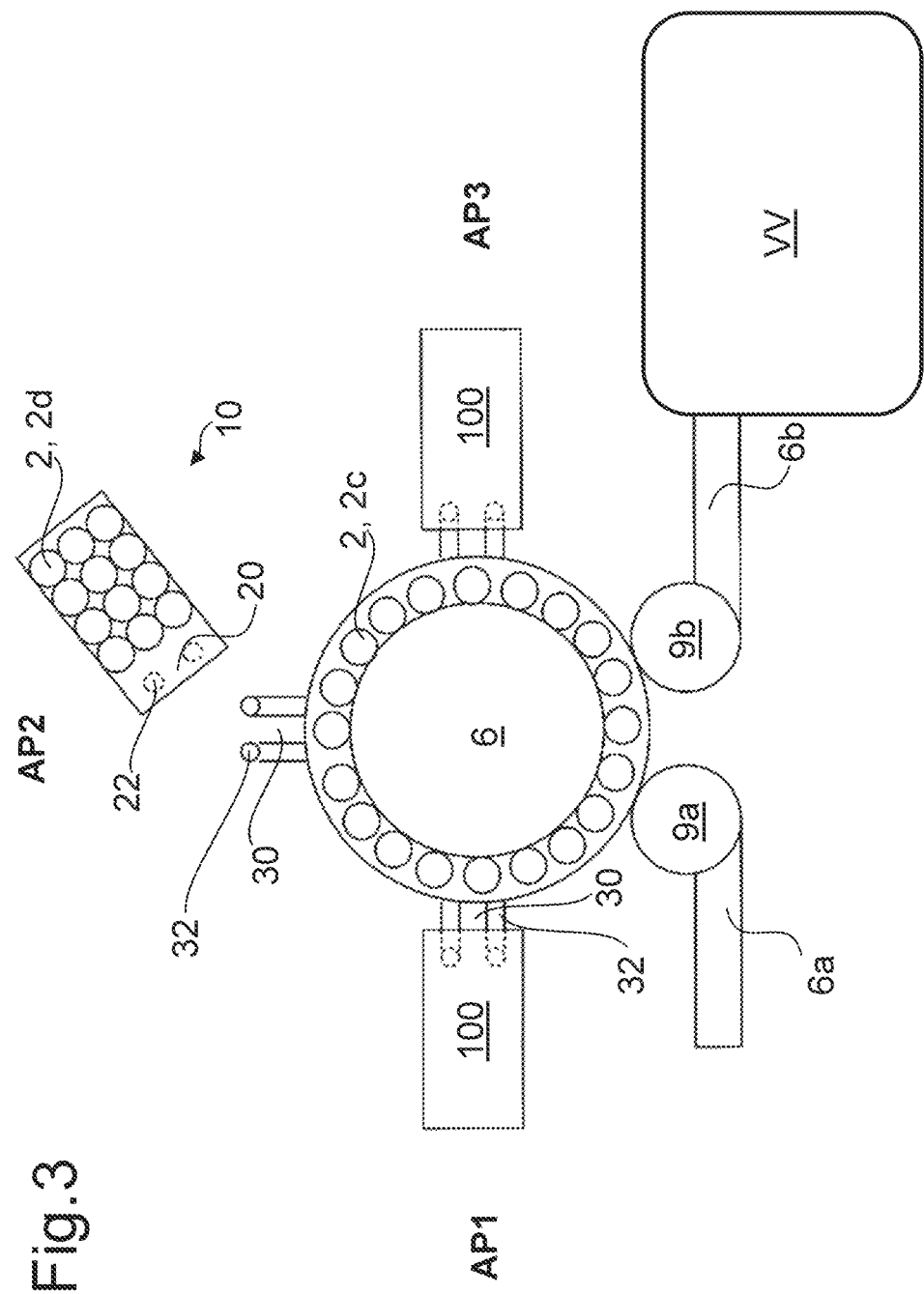
FIG. 3 shows an automatic exchange machine according to the invention being employed at a labeling module.

FIG. 3 shows an automatic exchange machine 10 according to the invention, which is being employed at a labeling module 6. The bottles to be labeled (not illustrated here) are transported by means of a feed conveyor 6a and an infeed star 9a to the labeling module 6 and conveyed to further processing devices VV by means of a removal conveyor 6b and an outfeed star 9b.

A number of different working tools 2 of the labeling module 6 require exchange and/or adaptation in the instance of a product change. Among these working tools are, for instance, the centering bells for clamping the bottles on the rotary tables; the rotary tables for turning the bottles around during labeling; the mandrels for expanding sleeve labels; the bars and/or their corresponding guide ducts or actuators for stretching the labels and pulling the labels over the bottles when using stretchable sleeve labels for labeling; the palettes for gluing and transporting labels from a retrieval magazine to a delivery point, glue containers with glue, the glue scrapers for scraping glue from the glue roller; the brushes for brushing the labels onto the bottles, the gripper cylinder for applying the labels to the bottles passing by; the vacuum cylinders for transporting and holding the labels for cutting when using web label material; feed screws; guide rails for bottles, mandrels, clamps, retainers for transporting bottles, controls for rotary tables (mechanical or electric), etc. In one embodiment form, in which the labeling machine is arranged between the blow molding machine and the filler, it is also necessary to exchange the base plates, for instance, which serve for supporting the bottle that is still hot from the blow molding process, wherein compressed air is used for pre-tensioning the bottle for the purpose of applying the label. It may furthermore be necessary to exchange the labels, too, and to provide appropriate magazines for individual labels or for rolls for endless labels, for instance sleeve or wraparound labels, or to exchange or provide printing units for printing labels or bottles on the spot, also including the appropriate print heads and their settings, printing ink containers, etc.

For instance, centering elements 32, which are already there, could be employed with the labeling module 6 itself for the labeling equipment 100 to enable the automatic exchange machine 10 to couple on by means of a corresponding interface 20. In particular, it may be provided that, instead of the labeling equipment 100, a plurality of automatic exchange machines 10 couple onto the labeling module 6 at respectively different working areas AP1, AP2, AP3 at the same time in order to simultaneously exchange and/or adapt a plurality of working tools 2, 2c, 2d. For performing a format change on the labeling equipment 100 itself, for instance an exchange of palettes, glue rollers, etc., the labeling equipment 100 may also be equipped with an appropriate connection device or with centering elements (not illustrated here).

Figure 4:
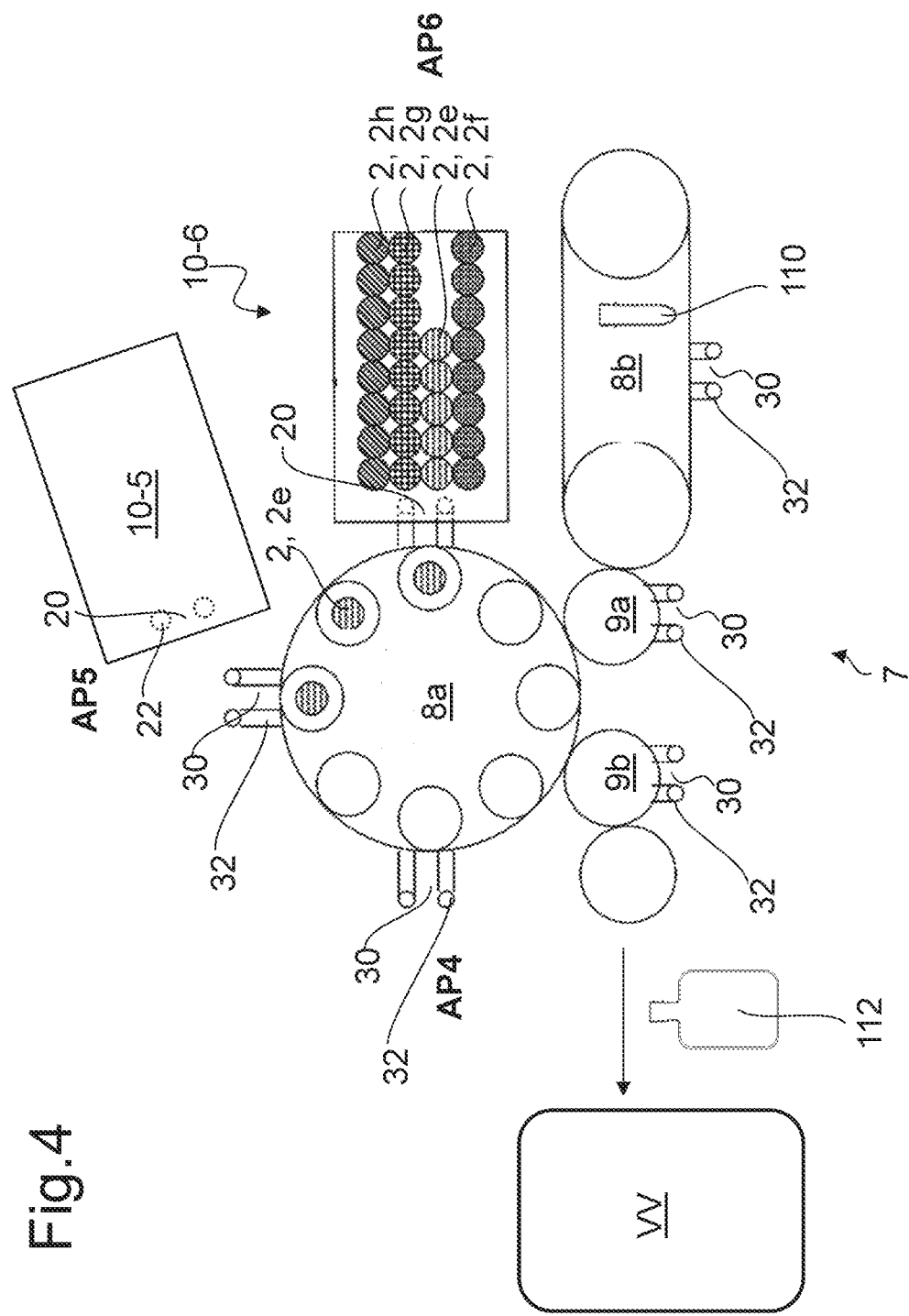
FIG. 4 shows an automatic exchange machine according to the invention being employed at a blow molding machine.

FIG. 4 shows a blowing device 7 with a plurality of automatic exchange machines 10 according to the invention being employed at the said blowing device 7. So-called preforms 110 are temperature-treated in a heating device 8b and fed to a blow molding module 8a via an infeed star 9a. In the blow molding module 8a, the preforms 110 are brought into the desired container form 112 by means of the proper blow mold 2e, 2f, 2g, or 2h, and fed to further processing devices VV via an outfeed star 9b.

A product change requires exchanging a number of working tools 2 or adapting a number of format parts in such a blowing device 7. In the heating device 8a, in a sterilization module located downstream, as the case may be, and/or in a preferential heating module located downstream, as the case may be, it may be necessary to exchange heating mandrels for transporting and heating the preforms 110, for instance. Various different shield panels are also employed. These shield panels serve for protecting the mouth sections of the preforms 110 from heat radiation while transporting the preforms 110 through the heating device 8b. The transport star clamps used for transporting the preforms 110 from the heating device 8b to a sterilization module, or to a preferential heating module for post-treatment, or immediately to a blow molding device 8a, or to the point where the bottles 112 are removed from the blow mold 2e, 2f, 2g, or 2h, also need to be adapted to the respective product. It may furthermore be necessary to exchange defective infrared lamps and/or reflectors and/or entire heater boxes comprising a multitude of lamps and/or filters in the heating device 8b.

In the blow molding module 8a itself, the blow molds 2, 2e need to be exchanged for other blow molds 2f, 2g, or 2h, for instance. In particular, the side parts and/or the insert trays and/or the base portions of the blow molds 2e, 2f, 2g, or 2h have to be exchanged here. Other working tools 2 to be exchanged or adapted include, for instance, the stretching rods or the tips of the stretching rods for longitudinally stretching the preforms 110 during the blowing process in the blow mold 2e, 2f, 2g, or 2h, the blowing nozzles for sealing the preforms 110 and for supplying the blowing air, the stop elements for the stretching rods, which serve for stopping the stretching rod shortly before it reaches the base of the blow mold in the stretching process, etc.

In such a blowing device 7, it may furthermore be necessary to adapt contact elements for temperature-treating the preforms 110 prior to entering the heating device 8b or between the heating device 8b and the blow molding module 8a in order to be able to perform, in particular, an adapted tempering treatment along the circumference direction of the preforms 110. Additionally, it may be necessary to exchange sterilization nozzles, preform guides, and/or injection molds. The injection molds obviously only have to be adapted in the instance of an injection molding device for producing the preforms 110 being connected upstream of the heating device 8b and the blow molding module 8a.

For the purpose of converting the diverse modules of a blowing device, each individual module—i.e. the heating device 8b, the blow molding module 8a, the infeed star 9a, the outfeed star 9b, etc.—may be provided with at least one connection device 30 having centering devices 32, which a correspondingly equipped automatic exchange machine 10 may be coupled to. According to the respective task, the automatic exchange machine 10 is equipped with the appropriate, above-described working tools 2 or with the necessary converting tools for adapting the format parts. It may furthermore be provided that a plurality of differently equipped automatic exchange machines 10 may be coupled to the blow molding module 8a in different working areas. For instance, an automatic exchange machine equipped with stretching rods (which is not illustrated here) may be coupled to the blow molding module 8a in the working area AP4, an automatic exchange machine 10-5 equipped with rod stops may be coupled in the working area APS, and an automatic exchange machine 10-6 equipped with blow molds 2e, 2f, 2g, or 2h may be coupled in the working area AP6, in this way making it possible to exchange three different working tools 2 at the same time.

Figure 5:
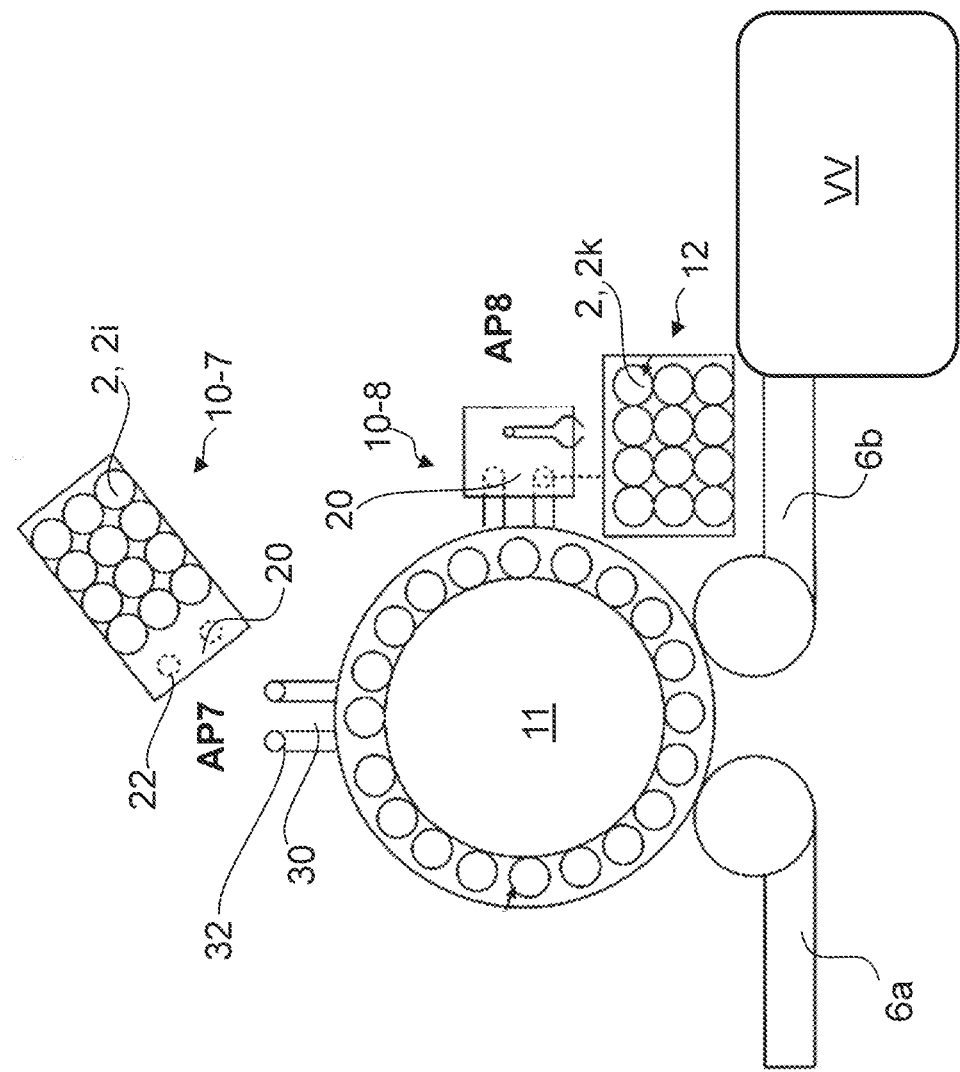
FIG. 5 shows an automatic exchange machine according to the invention being employed at a filler.

FIG. 5 shows a plurality of automatic exchange machines 10 according to the invention, said plurality of automatic exchange machines being employed at a filler 11. The bottles for filling are supplied to the filler 11 by a feed conveyor 6a and, after filling, they are supplied to a closing device, for instance, or to another processing device VV, by a removal conveyor 6b. The filler 11 itself or the other processing modules assigned to a filler, for instance devices for rinsing, sterilizing, and/or closing, may also require the exchange or adaptation of various working tools 2. The working tools that need to be adapted to the respective product may for instance comprise so-called electron beam fingers for sterilizing the bottles by means of electron beams; sterilization nozzles for sterilizing the bottles by chemical sterilization means, using, for instance, hydrogen peroxide ($H_2O_2$); rinse nozzles for rinsing the bottles with sterile water; after-cooling nozzles for removing heat from the bases of recently blown bottles and for hardening them; filling valves; filling pipes for filling the bottles, centering bells at the filling valve for centrally aligning the bottles during the filling process; return air pipes for removing the air from the container during the filling process; closing cones or closing heads for applying caps by placing, twisting, or pressing them onto the container mouths; feed screws, guide rails for the bottles, mandrels, clamps, groups of clamps, retainers for transporting bottles, etc.

An automatic exchange machine 10-7, which is appropriately equipped with neck handling clamps 2i, may be coupled to the filler 11 in a working area AP7, for instance, while an automatic exchange machine 10-8 for exchanging the filling valves 2k may be provided at the working area APB. One embodiment form of the invention may provide that the required working tools 2 are not always supplied by the automatic exchange machine 10 itself, but rather that the automatic exchange machine 10 retrieves these working tools 2 from an external magazine 12, which is stationary and allocated to the filler 11, for instance.

The external magazine 12 may comprise a connection similar to that at the individual modules or the automatic exchange machine may comprise additional connecting elements or centering elements in order to be able to dock onto external magazines.

Figure 6:
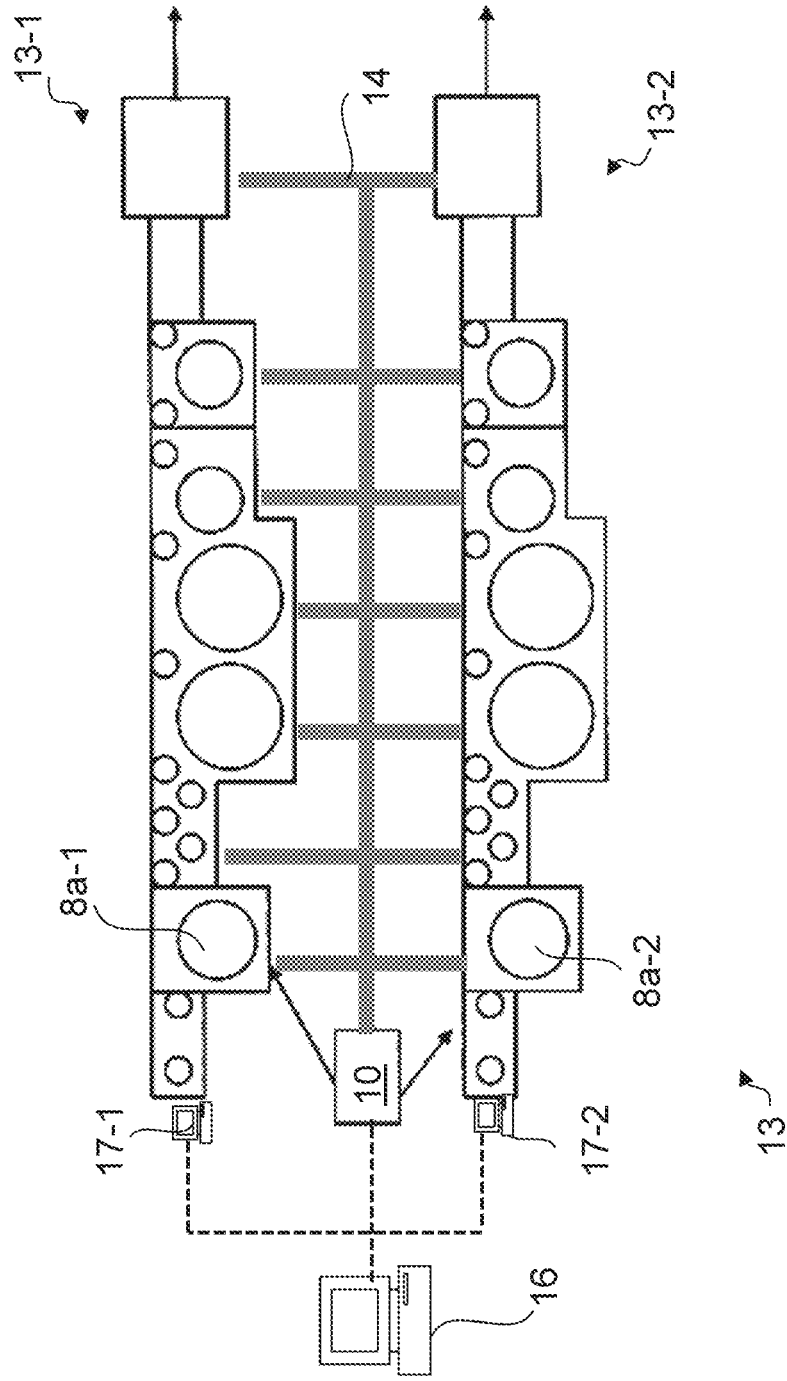
FIG. 6 shows an automatic exchange machine according to the invention being employed in a filling line.

FIG. 6 shows an automatic exchange machine 10 according to the invention, which automatic exchange machine 10 is being employed in a filling line 13 with at least two production lines 13-1, 13-2. Preferably, the production lines 13-1, 13-2 are employed for different products each and therefore require adaptation each at different points of time. It is intended to employ a mobile, automatic exchange machine 10 both at the blow molding module 8a-1 of the production line 13-1 and at the blow molding module 8a-2 of the production line 13-2, for instance. After the exchange of the working tools arranged in the magazine, it may furthermore be intended to employ the automatic exchange machine 10 in other modules of the production lines 13-1, 13-2, as well. According to one embodiment form, the automatic exchange machine also serves as a magazine for diverse working tools and/or tools at the same time. Alternatively, a specific automatic exchange machine 10 with blow molds, another automatic exchange machine specifically for heating mandrels, a further automatic exchange machine specifically intended for gripping clamps, etc. may be provided for each blow molding module 8a-1, 8a-2. A filling line 13 having at least two production lines 13-1, 13-2 is thus provided with a specific automatic exchange machine for each working tool 2, which automatic exchange machines perform the appropriate exchange or the appropriate adaptation of the respective production lines 13-1, 13-2 as required.

The automatic exchange machines 10 are each designed to be moveable, for instance in such a manner that an operator of the facility may move the automatic exchange machine 10 to the respective module and couple it onto the module. The automatic exchange machines 10 may alternatively move along a track system 14, preferably comprise their own drives, and be automatically controllable. In particular, the control device 16 of the automatic exchange machine is coupled to the respective control devices 17-1 and 17-2 of the production lines 13-1, 13-2. The control devices 17-1, 17-2 each store the production data of the respective production line 13-1, 13-2 that they are assigned to. The control device 16 coordinates the automatic exchange machine 10 by means of these data. The control device 16 may, in particular, be provided to signal to the operator of the facility in due time that the automatic exchange machine 10 requires to be equipped with new or different working tools 2 and/or new or different tools. The automatic exchange machine 10 may also be able to receive production orders, in particular wirelessly, and to perform them independently.

The connection created between the processing module 8a and the automatic exchange machine 10 at the working area, where the automatic exchange machine 10 is assigned to the respective processing module 8a, is not mandatorily a direct connection. The automatic exchange machine 10 may also be spatially assigned to a processing module 8a by means of corresponding connecting elements in the floor of the production hall. The automatic exchange machine 10 may also be provided with its own detection system for detecting the desired position at the processing module 8a. In particular, this may be an optical detection system. Alternatively, suitable electronic and/or magnetic systems or the like may serve for detection purposes.

Figure 7:
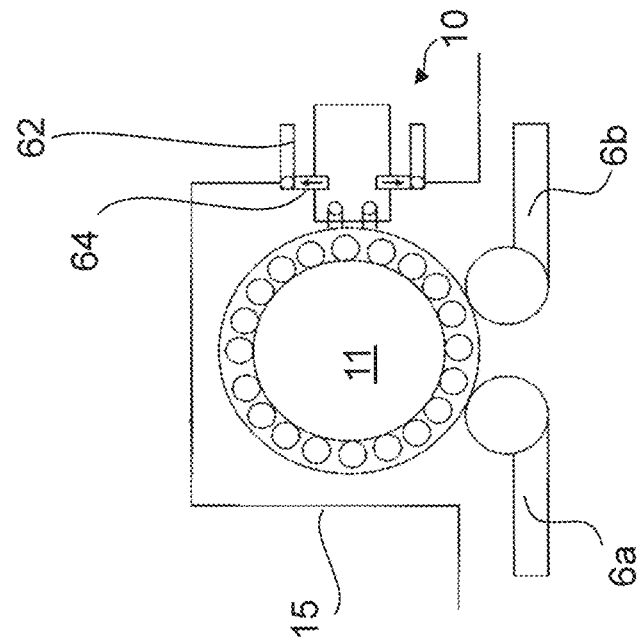
FIG. 7 and FIG. 8 show a further embodiment form for employing an automatic exchange machine according to the invention at a filler.
Figure 8:
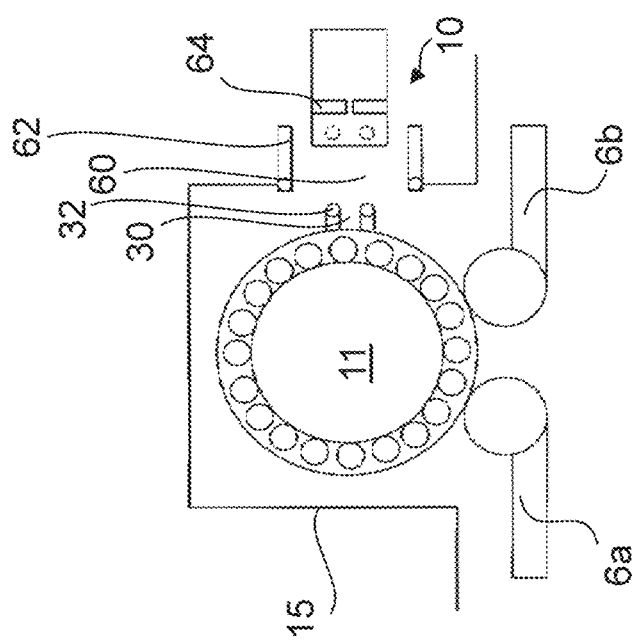

FIG. 7 and FIG. 8 show a further embodiment form for employing an automatic exchange machine 10 according to the invention at a filler 11. The filler 11 is preferably encased by a housing 15. The housing 15 serves as protection against dirt and pollutants from the outside. The housing 15 furthermore allows maintaining sterility of the filler. The housing has at least one exchange opening 60, which is closed by security doors 62. The security doors 62 are opened in the instance of a product change so that an automatic exchange machine 10, which is equipped with the appropriate working tools and/or the appropriate tools, may couple onto the appropriate connection device 30. The automatic exchange machine 10 preferably comprises security devices 64 for locking the safety doors 62 of the automatic exchange machine 10, as soon as it is coupled onto the filler 11. This prevents an operator from inadvertently reaching in between during the exchange process.

Figure 9:
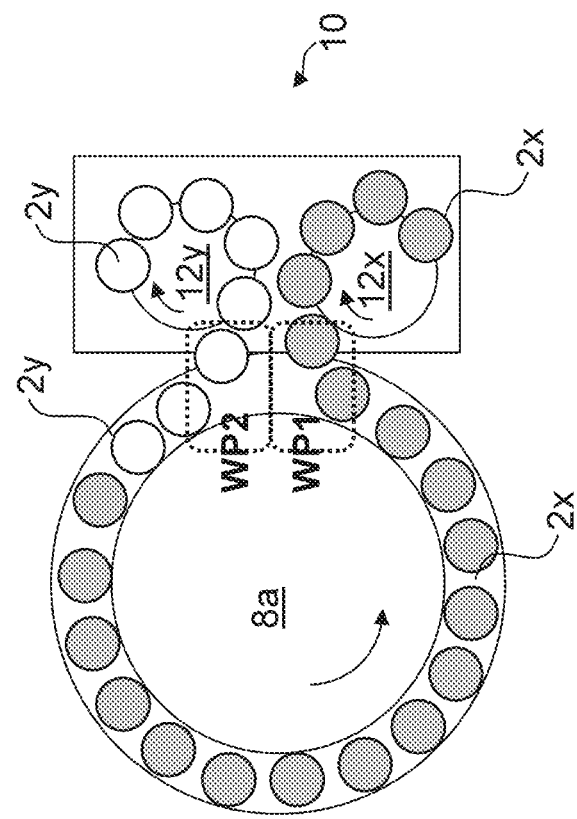
FIG. 9 shows a further embodiment form of an automatic exchange machine according to the invention.

FIG. 9 shows a further embodiment variant of the automatic exchange machine 10 according to the invention, which in particular enables a continuous exchange of working tools 2, 2x, 2y. In the present instance, such an automatic exchange machine 10 is shown as it is being employed at a blow molding module 8a. The automatic exchange machine 10 comprises at least one magazine 12x for the former working tools 2x, which are retrieved from the blow molding module 8a, and at least one further magazine 12y for the new working tools 2y. In particular, the automatic exchange machine 10 is intended to both retrieve a former working tool 2x at a first exchanging position WP1 and mount a new working tool 2y at a second, empty exchanging position WP2 at the same time. The retrieval of a former working tool 2x and the fastening of a new working tool 2y thus take place simultaneously. An exception is the retrieval of the first former working tool 2x in the beginning of the process. This initial retrieval necessarily precedes the synchronous exchange because it is not possible to mount a new working tool 2y in a position that is still filled by a former working tool 2x. In particular, the exchange is performed into rotating magazines 12x, 12y, where the working tools are spaced very closely together and in particular closer together than on the treatment device 8a. In order to keep the magazines 2x, 2y as small as possible, they may be designed so as to store objects in an upwardly spiraling arrangement. It is also conceivable that the automatic exchange machines perform the exchange in a continuous process, either at a reduced speed in relation to the regular production speed of the treatment device 8a or, ideally, even at production speed. In either case, it is intended to continue production during the exchange process. For this purpose, either one container may be discharged at the feed conveyor or earlier than that (or not be produced by the treatment device 8a in the first place) so as to prevent having a container for treatment in the gap resulting from removing the first working tool 2x. Theoretically, the container could be retrieved together with the working tool 2x, and the automatic exchange machine 10 would then discharge the container.

In this embodiment form, the working areas designated with WP1 and WP2 are arranged largely adjacent to each other on a single carousel of a blow molding module. According to the embodiment form illustrated in FIG. 9, the working areas designated with WP1 and WP2 are arranged immediately adjacent to each other on a carousel of the blow molding module and may be operated by means of one single automatic exchange machine 10.

FIG. 10a schematically shows a further embodiment variant wherein the automatic exchange machine comprises a robot with a plurality of arms and/or gripping tools. FIG. 10b schematically shows a further embodiment variant wherein the container treatment module is a blow molding module having a blowing wheel, an adjustable curve, and blow mold carriers.

The invention has been described with reference to a preferred embodiment. Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

LIST OF REFERENCE CHARACTERS

1 Processing device
2 Working tool, e.g. blow mold or heating mandrel
3 Lifting mechanism
4 Transfer device
5 Monotec transfer star wheel
6 Labeling module
6a/b Feed conveyor/Removal conveyor
7 Blowing device
8a Blow molding module
8b Heating device 9a/b Infeed star/Outfeed star
10 Automatic exchange machine
11 Filler
12 Magazine for working tools and/or tools
13 Filling line
13-1/13-2 Production line
14 Track system
15 Housing
16 Control device
17 Control device
18 Push handle
20 Interface
22 Centering opening
24 Electrical connecting elements
30 Connection point
32 Centering pin/Centering cone
34 Electrical connecting elements
40 Wheels
44 Sensor
46 Display panel
48 Control unit
50 Battery
52 Drive
60 Exchange opening
62 Safety door
64 Safety device
100 Labeling equipment
110 Preform
112 Container/Bottle
AP Working area
VV Processing device
WP Exchanging position

I claim:

1. A container treatment system (1, 13) for producing or processing products or groups of products, the container treatment system (1, 13) comprising:
   at least two different container treatment modules, each having: (i) at least one working area (AP) with at least one exchangeable working tool (2) located at an exchange position on the at least one working area, or (ii) at least one adaptable format part located at an exchange position on the at least one working area (AP); and
   at least one automatic exchange machine (10) that is movable to each working area (AP), wherein the at least one automatic exchange machine (10) is capable of exchanging the at least one exchangeable working tool (2) at each exchange position or adapting the at least one adaptable format part at each exchange position,
   and wherein one of the at least two container treatment modules operates, during an exchange cycle for the one of the at least two container treatment modules, in an intermittent, strokewise manner;
   and wherein, per stroke of the one of the at least two container treatment modules during the exchange cycle, the at least one automatic exchange machine (10) retrieves one exchangeable working tool (2) from the exchange position and stores it in a magazine,
   and wherein, on a subsequent stroke of the one of the at least two container treatment modules during the exchange cycle, the at least one automatic exchange machine (10) mounts one exchangeable working tool (2) at the exchange position, wherein the at least one exchangeable working tool (2) is a blow mold.

2. The container treatment system (1, 13) as recited in claim 1 wherein each working area (AP) includes at least one first connection device (30) with a centering device (32) and wherein the at least one automatic exchange machine (10) includes at least one second connection device (20) with a centering opening (22),
   wherein the at least one second connection device (20) with a centering opening (22) of the at least one automatic exchange machine (10) is formed correspondingly to the first connection device (30) with the centering device (32) of each of the at least two working areas (AP) and
   wherein the first connection device (30) with the centering device (32) and the second connection device (20) with the centering opening (22) together form a connection between one of the working areas (AP) and the at least one automatic exchange machine (10).

3. The container treatment system (1, 13) as recited in claim 2 wherein the at least one automatic exchange machine (10) comprises at least one magazine (12) for working tools (2).

4. The container treatment system (1, 13) as recited in claim 3 wherein the at least one automatic exchange machine (10) comprises a transport means (40).

5. The container treatment system (1, 13) as recited in claim 4 further comprising a system of tracks (14) extending between each of the at least two working areas (AP) and wherein the at least one automatic exchange machine (10) is moveable along the system of tracks (14) between each of the at least two working areas (AP).

6. The container treatment system (1, 13) as recited in claim 5 wherein the at least one automatic exchange machine (10) comprises a control device (48) and wherein the control device (48) controls the exchange of the working tools (2) at each of the working areas (AP) and/or the adaptation of the at least one adaptable format part at each of the working areas (AP) and/or the positioning of the automatic exchange machine (10) at each of the working areas (AP).

7. The container treatment system (1, 13) as recited in claim 6 further comprises a control device (16, 17) and wherein the at least one automatic exchange machine (10) may be coupled to at least one of the at least two different container treatment modules (5, 8, 11).

8. The container treatment system (1, 13) as recited in claim 7 wherein the at least one automatic exchange machine (10) and the at least two different container treatment modules comprise interfaces for supplying power, compressed air, and/or data to the at least one automatic exchange machine (10).

9. The container treatment system (1, 13) as recited in claim 8 wherein the at least one automatic exchange machine (10) further comprises a detection system including a sensor (44) for detecting working tools (2).

10. The container treatment system (1, 13) as recited in claim 9 wherein the at least one automatic exchange machine (10) comprises at least one empty magazine (12x) for receiving working tools (2x) after removal from one of the container treatment modules and comprises at least one storage magazine (12y), into which the working tools (2y) for being mounted can be filled, and wherein the at least one automatic exchange machine (10) may perform the removal of the working tools (2x) and the mounting of the working tools (2y) simultaneously.

11. The container treatment system (1, 13) as recited in claim 4 wherein the transport means (40) comprises a drive (50) for moving the at least one automatic exchange machine (10) from a first of the working areas (AP) to a second of the working areas (AP).

12. The container treatment system (1, 13) as recited in claim 1 wherein the at least one automatic exchange machine (10) comprises at least one second connection device (20) with a centering opening (22), and wherein each of the working areas (AP) include at least one first connection device (30) with a centering device (32), wherein the at least one second connection device (20) with the centering opening (22) of the at least one automatic exchange machine (10) is formed correspondingly to each first connection device (30) with the centering device (32) of each of the two working areas (AP), and wherein a connection can be created between each of the working areas (AP) and the at least one automatic exchange machine (10), and wherein the at least one automatic exchange machine (10) is mobile and employable at each of the working areas (AP).

13. The container treatment system (1, 13) as recited in claim 12 wherein the at least one automatic exchange machine (10) comprises at least one empty magazine (12*x*) for receiving working tools (2*x*) after removal from one of the container treatment modules and at least one storage magazine (12*y*), into which the working tools (2*y*) for being mounted can be filled, and wherein the at least one automatic exchange machine (10) may perform the removal of the working tools (2*x*) and the mounting of the working tools (2*y*) simultaneously.

14. The container treatment system (1, 13) as recited in claim 12 wherein the at least one automatic exchange machine (10) comprises at least one empty magazine (12*x*) for receiving working tools (2*x*) after removal from one of the container treatment modules and at least one storage magazine (12*y*), into which the working tools (2*y*) for being mounted can be filled.

15. The container treatment system (1, 13) as recited in claim 14, wherein the magazines (12*x*, 12*y*) are continuously advanced.

16. The container treatment system (1, 13) as recited in claim 14 wherein the magazines (12*x*, 12*y*) are continuously rotated.

17. The container treatment system (1, 13) as recited in claim 1 wherein one of the container treatment modules comprise a blowing wheel and an adjustable curve, wherein the adjustable curve, in an exchange mode, unlocks and opens blow mode carriers to permit exchange of blow molds, and wherein the adjustable curve, in operation mode, retracts from interacting with the blow mold carriers.

18. The container treatment system (1, 13) as recited in claim 1 wherein the at least one automatic exchange machine (10) is drivable to the at least two working areas (AP).

19. The container treatment system (1, 13) as recited in claim 1 further comprising an external magazine that is separate from the at least one automatic exchange machine (10).

20. A container treatment system (1, 13) for producing or processing products or groups of products, the container treatment system (1, 13) comprising:

at least two different container treatment modules, each having: (i) at least one working area (AP) with at least one exchangeable working tool (2) located at an exchange position on the at least one working area, or (ii) at least one adaptable format part located at an exchange position on the at least one working area (AP); and at least one automatic exchange machine (10) that is movable to each working area (AP), wherein the at least one automatic exchange machine (10) is capable of exchanging the at least one exchangeable working tool (2) at each exchange position or adapting the at least one adaptable format part at each exchange position, and wherein one of the at least two container treatment modules operates, during an exchange cycle for the one of the at least two container treatment modules, in an intermittent, strokewise manner;

and wherein, per strike of the one of the at least two container treatment modules during the exchange cycle, the at least one automatic exchange machine (10) retrieves one exchangeable working tool (2) from the exchange position and stores it in a magazine, and wherein, on a subsequent stroke of the one of the at least two container treatment modules during the exchange cycle, the at least one automatic exchange machine (10) mounts one exchangeable working tool (2) at the exchange position, wherein the at least one exchangeable working tool (2) is a blow mold;

and wherein for another one of the at least two container treatment modules, the at least one automatic exchange machine (10) exchanges a mandrel for transporting and heating preforms.

\* \* \* \* \*